US008728777B2

(12) United States Patent
Biton et al.

(10) Patent No.: US 8,728,777 B2
(45) Date of Patent: May 20, 2014

(54) HIGH PERFORMANCE METABOLIC BACTERIA

(75) Inventors: Jacques Biton, Lacroix-Saint-Ouen (FR); Cathy Isop, Gallargues le Montueux (FR)

(73) Assignees: Deinove, Paris (FR); Centre Naitonal de la Recherche Scientifique, Paris (FR); Universite Montpellier I, Montpellier Cedex 2 (FR)

( * ) Notice: Subject to any disclaimer, the term of this patent is extended or adjusted under 35 U.S.C. 154(b) by 0 days.

(21) Appl. No.: 13/320,048

(22) PCT Filed: May 12, 2010

(86) PCT No.: PCT/EP2010/056600
§ 371 (c)(1),
(2), (4) Date: Nov. 11, 2011

(87) PCT Pub. No.: WO2010/130812
PCT Pub. Date: Nov. 18, 2010

(65) Prior Publication Data
US 2012/0052540 A1    Mar. 1, 2012

(30) Foreign Application Priority Data
May 14, 2009    (EP) .................................... 09160287

(51) Int. Cl.
*C12N 1/20*    (2006.01)

(52) U.S. Cl.
USPC ..................... 435/139; 435/140; 435/252.1

(58) Field of Classification Search
USPC ............... 435/161, 132, 170, 252.3
See application file for complete search history.

(56) References Cited

U.S. PATENT DOCUMENTS

| | | | |
|---|---|---|---|
| 6,102,690 A | 8/2000 | Ingram et al. | |
| 2011/0104766 A1* | 5/2011 | Leonetti et al. | ............... 435/132 |
| 2011/0294979 A1 | 12/2011 | Leonetti et al. | |
| 2011/0306085 A1 | 12/2011 | Isop et al. | |
| 2012/0058533 A1 | 3/2012 | Biton et al. | |

FOREIGN PATENT DOCUMENTS

| | | |
|---|---|---|
| EP | 2218773 | 8/2010 |
| KR | 100836093 | 6/2008 |
| WO | WO 95/27064 | 10/1995 |
| WO | WO 97/10352 | 3/1997 |
| WO | WO 01/23526 | 4/2001 |
| WO | WO 02/059351 | 8/2002 |
| WO | WO 2006/131734 | 12/2006 |
| WO | WO 2007/128338 | 11/2007 |
| WO | WO 2009/063079 | 5/2009 |
| WO | WO 2010/081899 | 7/2010 |
| WO | WO 2010/094665 | 8/2010 |
| WO | WO 2010/130806 | 11/2010 |
| WO | WO 2011/107506 | 9/2011 |

OTHER PUBLICATIONS

*Deinococcus radiodurans*-the consummate survivor. Cox et al., Nature Reviews in Microbiology, 3: 882-892, 2005.*
Anonymous. "Conference de presse: Présentation des projets de DEINOVE dans le domaine des biocarburants et des activités de DEINOLAB, laboratoire coopératif créé par DEINOVE, le CNRS et l'Université de Montpellier" Oct. 15, 2008, pp. 1-10.
Weon, H. et al. "*Deinococcus cellulosilyticus* sp. nov., isolated from air" *International Journal of Systematic and Evolutionary Microbiology*, Aug. 1, 2007, pp. 1685-1688, vol. 57, No. Part 8.
Ferreira, A. et al. "*Deinococcus geothermalis* sp. nov. and *Deinococcus murrayi* sp. nov., Two Extremely Radiation-Resistant and Slightly Thermophilic Species from Hot Springs" *International Journal of Systematic Bacteriology*, Oct. 1997, pp. 939-947, vol. 47, No. 4.
Kolari, M. et al. "Colored moderately thermophilic bacteria in paper-machine biofilms" *Journal of Industrial Microbiology and Biotechnology*, Apr. 2003, pp. 225-238, vol. 30, No. 4.
Written Opinion in International Application No. PCT/EP2010/056600, May 14, 2009, pp. 1-8.
Harish, V. et al. "Xylanase Production by Ultra Violet Induced Variants of *Streptomyces fradiae* SCF-5" *Journal of Food Science and Technology*, Jan. 1, 1978, pp. 243-246, vol. 15, No. 6.
Alea, F. et al. "Selection of hypercellulolytic derepressed mutants of *Cellulomonas* sp." *Applied Microbiology and Biotechnology*, 1991, pp. 643-645, vol. 35, No. 5.
Temp, U. et al. "A Small-Scale Method for Screening of Lignin-Degrading Microorganisms" *Applied Environmental Microbiology*, Apr. 1998, pp. 1548-1549, vol. 64, No. 4.
Zenoff, V. F. et al. "Diverse UV-B Resistance of Culturable Bacterial Community from High-Altitude Wetland Water" *Current Microbiology*, May 1, 2006, pp. 359-362, vol. 52, No. 5.
Pavlikova, E. et al. "Improvement of the Basidiomycete *Coprinus* sp." *Folia Microbiologica*, Jan. 1, 1982, pp. 126-130, vol. 27, No. 2.
Written Opinion in International Application No. PCT/EP2010/051885, Aug. 23, 2010, pp. 1-10.
Makarova, K. et al. "Genome of the Extremely Radiation-Resistant Bacterium *Deinococcus radiodurans* Viewed from the Perspective of Comparative Genomics" *Microbiology and Molecular Biology Reviews*, Mar. 2001, pp. 44-79, vol. 65, No. 1.
Omelchenko, M. et al. "Comparative genomics of *Thermus thermophilus* and *Deinococcus radiodurans*: divergent routes of adaptation to thermophily and radiation resistance" *BMC Evolutionary Biology*, 2005, pp. 1-22, vol. 5, No. 57.
Rainey, F. et al. "Extensive Diversity of Ionizing-Radiation-Resistant Bacteria Recovered from Sonoran Desert Soil and Description of Nine New Species of the Genus *Deinococcus* Obtained from a Single Soil Sample" *Applied and Environmental Microbiology*, Sep. 2005, pp. 5225-5235, vol. 71, No. 9.

(Continued)

*Primary Examiner* — Tekchand Saidha
*Assistant Examiner* — Rama P Ramanujam
(74) *Attorney, Agent, or Firm* — Saliwanchik, Lloyd & Eisenschenk

(57) ABSTRACT

The present invention relates to novel stress-resistant bacteria and the uses thereof. More specifically, the invention relates to isolated stress-resistant bacteria having advantageous properties for the production of organic acids or alcohols in various culture conditions. The invention also relates to methods of producing organic acids or alcohols using said bacteria, particularly from biomass.

16 Claims, No Drawings

(56) References Cited

OTHER PUBLICATIONS

Weisburg, W.G. et al. "The *Deinococcus-Thermus* Phylum and the Effect of rRNA Composition on Phylogenetic Tree Construction" *Systematic and Applied Microbiology*, 1989, pp. 128-134, vol. 11.

Database EMBL, Accession No. M21413, "D. radiodurans 16s ribosomal RNA gene" XP002633260, Nov. 23, 1989, p. 1.

Suihko, M.L. et al. "Characterization of aerobic bacterial and fungal microbiota on surfaces of historic Scottish monuments" *Systematic and Applied Microbiology*, 2007, pp. 494-508, vol. 30.

Database EMBL, Accession No. EF093134, "*Deinococcus* sp. VTT E-052909 16S ribosomal RNA gene, complete sequence" XP002633261, Aug. 7, 2007, pp. 1-2.

Database EMBL, Accession No. AM283039, "*Deinococcus* sp. Han23 partial 16S rRNA gene, strain Han23" XP002633262, Jun. 26, 2006, p. 1.

Rainey, F. et al. "Phylogenetic Diversity of the *Deinococci* as Determined by 16S Ribosmal DNA Sequence Comparison" *International Journal of Systemic Bacteriology*, Apr. 1997, pp. 510-514, vol. 47, No. 2.

Written Opinion in International Application No. PCT/EP2011/053089, Mar. 2, 2010, pp. 1-7.

Brim, H. et al. "Engineering *Deinococcus radiodurans* for metal remediation in radioactive mixed waste environments" *Nature Biotechnology*, Jan. 2000, pp. 85-90, vol. 18, XP-002491111.

Henstra, A. M. et al. "Microbiology of synthesis gas fermentation for biofuel production" *Current Opinion in Biotechnology*, 2007, pp. 200-206, vol. 18, XP-22110181.

John, R. P. et al. "Fermentative production of lactic acid from biomass: an overview on process developments and future perspectives" *Appl. Microbiol. Biotechnol.*, 2007, pp. 524-534, vol. 74, XP-002464997.

Klapatch, T. R. et al. "Organism Development and Characterization for Ethanol Production Using Thermophilic Bacteria" *Applied Biochemistry and Biotechnology*, 1994, pp. 209-223, vol. 45/46, XP-009104255.

Lynd, L. R. "Production of Ethanol from Lignocellulosic Materials Using Thermophilic Bacteria: Critical Evaluation of Potential and Review" *Advances in Biochemical Engineering*, 1989, pp. 1-52, vol. 38, XP-9104256.

Makarova, K. S. et al. "*Deinococcus geothermalis*: The Pool of Extreme Radiation Resistance Genes Shrinks" *PLOS ONE*, Sep. 2007, pp. 1-21, vol. 9, XP-002491112.

Meima, R. et al. "Promoter Cloning in the Radioresistant Bacterium *Deinococcus radiodurans*" *Journal of Bacteriology*, May 2001, pp. 3169-3174, vol. 183, No. 10, XP-002491110.

Smith, M. D. et al. "Gene expression in *Deinococcus radiodurans*" *Gene*, 1991, pp. 45-52, vol. 98, XP-002938523.

Zahradka, K. et al. "Reassembly of shattered chromosomes in *Deinococcus radiodurans*" *Nature*, Oct. 5, 2006, pp. 569-573, vol. 443, XP-002491114.

Office Action dated Nov. 8, 2012 in U.S. Appl. No. 12/740,404.

Fontaine, L. et al. "Molecular Characterization and Transcriptional Analysis of adhE2, the Gene Encoding the NADH-Dependent Aldehyde/Alcohol Dehydrogenase Responsible for Butanol Production in Alcohologenic Cultures of *Clostridium acetobutylicum* ATCC 824" *Journal of Bacteriology*, Feb. 2002, pp. 821-830, vol. 184, No. 3.

Skory, C. D. "Isolation and Expression of Lactate Dehydrogenase Genese from *Rhizopus oryzae*" *Applied and Environmental Microbiology*, Jun. 2000, pp. 2343-2348, vol. 66, No. 6.

Berdy, J. "Bioactive Microbial Metabolites—A personal view" *Journal of Antibiotics*, Jan. 1, 2005, pp. 1-26, vol. 58, No. 1.

Singh, S. et al. "Biodiversity, chemical diversity and drug discovery" *Progress in Drug Research*, 2008, pp. 142-174, vol. 65.

Yang, B. et al. "Effects of microwave irradiation on isolation of soil actinomycetes" *Yingyong Shengtai Xuebao*, May 2008, pp. 1091-1098, vol. 19, No. 5.

Sinha, R. et al. "UV-protectants in cyanobacteria" *Plant Science*, Dec. 23, 2007, pp. 278-289, vol. 174, No. 3.

Chung, B. et al. "Effects of low-dose gamma-irradiation on production of shikonin derivatives in callus cultures of *Lithospermum erythrorhizon* S." *Radiation Physics and Chemistry*, Sep. 1, 2006, pp. 1018-1023, vol. 75, No. 9.

Ghosal, D. et al. "How radiation kills cells: Survival of *Deinococcus radiodurans* and *Shewanella oneidensis* under oxidative stress" *FEMS Microbiology Reviews*, Apr. 2005, pp. 361-375, vol. 29.

Dib, J. et al. "Occurrence of Resistance to Antibiotics, UV-B, and Arsenic in Bacteria Isolated from Extreme Environments in High-Altitude (Above 4400 m) Andean Wetlands" *Current Microbiology*, May 2008, pp. 510-517, vol. 56, No. 5.

Keller, M. et al. "Tapping Into Microbial Diversity" *Nature Reviews*, Feb. 2004, pp. 141-150, vol. 2, No. 2.

Reichenbach, H. "Myxobacteria, producers of novel bioactive substances" *Journal of Industrial Microbiology & Biotechnology*, Jan. 1, 2001, pp. 149-156, vol. 27. No. 3.

Bibb, M. "Regulation of secondary metabolism in streptomycetes" *Current Opinion in Microbiology*, 2005, pp. 208-215, vol. 8, No. 2.

Written Opinion in International Application No. PCT/EP2010/050513, Apr. 24, 2010, pp. 1-10.

Zhang, Y.-M. et al. "Induction of a Futile Embden-Meyerhof-Parnas Pathway in *Deinococcus radiodurans* by Mn: Possible Role of the Pentose Phosphate Pathway in Cell Survival" *Applied and Environmental Microbiology*, Jan. 2000, pp. 105-112, vol. 66, No. 1.

Holland, A. et al. "Development of a defined medium supporting rapid growth for *Deinococcus radiodurans* and analysis of metabolic capacities" *Applied Microbiology and Biotechnology*, Mar. 31, 2006, pp. 1074-1082, vol. 72, No. 5.

Written Opinion in International Application No. PCT/EP2010/056592, Jul. 29, 2010, pp. 1-7.

Written Opinion in International Application No. PCT/EP2008/065613, Jan. 28, 2009, pp. 1-8.

\* cited by examiner

HIGH PERFORMANCE METABOLIC BACTERIA

CROSS-REFERENCE TO RELATED APPLICATION

This application is the U.S. national stage application of International Patent Application No. PCT/EP2010/056600, filed May 12, 2010.

The present invention relates to novel bacteria and the uses thereof. More specifically, the invention relates to isolated stress-resistant bacteria, particularly *Deinococcus* bacteria, having advantageous properties for the production of organic acids or alcohols in various culture conditions. The invention also relates to methods of producing organic acids or alcohols using said bacteria, particularly from biomass.

INTRODUCTION

Bacteria having the capacity to reassemble their genome when disrupted by a stress have been reported in the literature, such as *Deinococcus* bacteria. *Deinococcus* is a gram positive bacterium that was isolated in 1956 by Anderson and collaborators. This extremophile organism is resistant to DNA damage by UV and ionizing radiations or by cross-linking agent (mitomycin C) and is tolerant to dessication.

WO01/023526 shows the unusual resistance of *Deinococcus* to radiation and further proposes their engineering and use in bioremediation. Patent application n° PCT/EP2008/065613, presently unpublished, shows that *Deinococcus* bacteria can resist to solvents and transform biomass to generate ethanol.

Other stress-resistant bacteria are disclosed in patent application EP 09 305041.7, presently unpublished, as well as methods for their isolation and/or selection, and their ability to produce metabolites such as antibiotics.

The present invention results from the isolation and characterization of novel stress-resistant bacteria having remarkable properties for the production of organic acids or alcohols. More particularly, the present invention discloses the isolation of novel stress-resistant bacteria that can utilize various carbon sources to produce organic acids or alcohols of high industrial interest. The invention discloses such strains, that have been isolated by the inventors, and can utilize a remarkably broad spectrum of carbon sources and/or have unexpected ability to generate organic acids or alcohols, particularly ethanol. The invention relates to such isolated bacteria and the uses thereof, particularly for producing organic acids or alcohols.

SUMMARY OF THE INVENTION

A first object of this invention relates to an isolated stress-resistant bacterium, particularly a *Deinococcus* bacterium, wherein said bacterium can utilize cellulose as a carbon source to produce an organic acid or alcohol in aerobiosis. In a preferred embodiment, the bacterium is thermophilic (i.e., viable at a temperature of 45° C. or more) and viable at a pH comprised between 5 and 9.

Another object of this invention is an isolated stress-resistant bacterium, particularly a *Deinococcus* bacterium, wherein said bacterium is thermophilic, viable at a pH comprised between 5 and 9, and produces at least 2 g/L of lactate.

A further object of this invention resides in an isolated stress-resistant bacterium, particularly a *Deinococcus* bacterium, wherein said bacterium is thermophilic, viable at a pH comprised between 5 and 9, and produces at least 0.05 g/L of succinate.

Another object of this invention is an isolated stress-resistant bacterium, particularly a *Deinococcus* bacterium, wherein said bacterium is thermophilic, viable at a pH comprised between 5 and 9, and produces at least 0.25 g/L of acetate.

Most preferred bacteria of this invention produce at least 0.004%, most preferably at least 0.04% ethanol.

The invention also relates to isolated stress-resistant bacteria, particularly *Deinococcus* bacteria, wherein said bacteria produce above 0.04% ethanol when cultured in aerobiosis in the presence of a carbon source, more preferably in the presence of cellulose as carbon source.

In a further aspect, the present invention relates to isolated stress-resistant bacteria, particularly *Deinococcus* bacteria, as defined above, which can further utilize additional substrates as carbon sources, particularly glucose, starch and sucrose.

Preferred bacteria of this invention can also utilize, as carbon source, carboxymethylcellulose, cellobiose, hemicellulose and xylose.

The invention indeed discloses the isolation of stress-resistant bacteria, particularly *Deinococcus* bacteria, having the remarkable capacity to utilize a very large spectrum of substrates as carbon source. Particular bacteria of this invention are *Deinococcus* bacteria, which may be selected from e.g., *D. radiodurans*, *D. geothermalis*, *D. murrayi*, *D. cellulosilyticus* or *D. deserti*. Specific examples of such bacteria include *Deinococcus* strain M11-9D, deposited on May 7, 2009 at the CNCM (Collection Nationale de Cultures de Microorganismes—Institut Pasteur, 25. Rue du Docteur Roux, F-75724 Paris Cedex 15, France) under No. CNCM I-4155; *Deinococcus* strain MC2-2A, deposited on May 7, 2009, at the CNCM under No. CNCM I-4156, and *Deinococcus* strain M13-1A, deposited on May 7, 2009 at the CNCM under No. CNCM I-4157, or a derivative, mutant, transformant or progeny of said bacterium.

A further object of this invention is a method of producing an organic acid or an alcohol, particularly ethanol, comprising cultivating a bacterium as disclosed above in the presence of an appropriate carbon source, and collecting the organic acid or alcohol.

A further object of this invention resides in the use of a bacterium as defined above for producing a bioalcohol, preferably ethanol.

The invention also relates to a culture device or a fermentor comprising a bacterium as disclosed above.

DETAILED DESCRIPTION OF THE INVENTION

The present invention relates to stress-resistant bacteria and the uses thereof for producing organic acids or alcohols.

Within the context of this invention, the term "stress-resistant bacterium" designates more specifically a bacterium having the capacity to reassemble its genome, in full or in part, when disrupted by a stress. The stress may be any cell-destructing DNA damaging treatment, i.e., a treatment that is sufficient to cause 90% cell death, or more, in a culture of *E. coli* bacteria. Even more preferably, the cell destructing DNA damaging treatment is a treatment that is sufficient to reduce by at least 2 log the bacterial titer in a culture of *E. coli*. Examples of such treatment include irradiation, preferably repeated and sequential UV irradiation, and/or the use of genotoxic agents. A preferred stress treatment is a UV treatment of between 0.5 and 400 mJ/cm2, more preferably of between 1 and 200 mJ/cm2, typically between 1 and 100 mJ/cm2, applied for a period of time of about 5" to 5'. A preferred UV treatment is 4 mJ/cm2 for 30 seconds, which may be repeated at an interval of between 1 and 8 hours, preferably 3 to 5 hours, and more preferably of about 4 hours. Specific cell stress treatments according to the invention have been described in patent application EP09 305041.7, unpublished, which is incorporated therein by reference.

Cell-stress resistant bacteria according to the present invention include more specifically *Deinococcus* bacteria, *Tepidimonas* bacteria, *Truepera* bacteria, *Porphyrobacter* bacteria, *Novosphingobium* bacteria or *Exiguobacterium* bacteria. Preferred bacteria of this invention are *Deinococcus* bacteria, particularly extremophile *Deinococcus* bacteria, more preferably *Deinococcus* bacteria selected from *D. radiodurans, D. geothermalis, D. murrayi, D. cellulosilyticus* or *D. deserti*.

*Deinococcus* bacteria have been shown to have the capacity to reassemble their genome, in full or in part, when disrupted by a stress. As previously mentioned, these bacteria, particularly *D. radiodurans*, have been proposed for bioremediation. The ability of *Deinococcus* bacteria to produce bioenergy products from biomass is disclosed in PCT/EP2008/065613, presently unpublished. The present invention now results from the identification and characterization of high performance stress-resistant bacteria. More particularly, the invention provides isolated stress-resistant bacteria, particularly *Deinococcus* bacteria, that have been isolated by the inventors from environmental samples, having improved performance for the production of organic acids or alcohols, particularly in relation to carbon source utilization and/or production levels.

Within the context of the present invention, the term organic acids designate, more preferably, an organic acid selected from formate, acetate, lactate, butyrate, gluconate, citrate, succinate, propionate, fumarate, malate, pyruvate, itaconic acid and kojic acid. More preferably, the isolated bacteria of this invention produce at least one, more preferably at least 2 of the above organic acids. Most preferred bacteria of this invention produce pyruvate, lactate, succinate, acetate, formate and/or malate.

In this regard, a preferred bacterium of this invention is a stress-resistant bacterium, particularly a *Deinococcus* bacterium, that produces at least 0.1 g/L of lactate, more preferably at least 0.5 g/L, even more preferably at least 0.8 g/L, most preferably at least 2 g/L of lactate.

Another preferred bacterium of this invention is a stress-resistant bacterium, particularly a *Deinococcus* bacterium, that produces at least 0.05 g/L of succinate.

Another preferred bacterium of this invention is a stress-resistant bacterium, particularly a *Deinococcus* bacterium, that produces at least 0.25 g/L of acetate.

Another preferred bacterium of this invention is a stress-resistant bacterium, particularly a *Deinococcus* bacterium, that produces formate or malate.

Within the context of this invention, the term alcohol designates more preferably ethanol, butanol, propanol, methanol, isopropanol, propanediol, glycerol, or 2-3 butane diol, preferably ethanol.

In this respect, a preferred bacterium of this invention is a stress-resistant bacterium, particularly a *Deinococcus* bacterium, that produces at least 0.004%, more preferably at least 0.015%, most preferably at least 0.04% ethanol. % ethanol designates g ethanol per g of culture medium (i.e., typically 1% ethanol=1 g ethanol/100 g medium=10 g ethanol/L).

As disclosed in the experimental section, stress-resistant bacteria, particularly *Deinococcus* bacteria, having such properties have now been isolated, which are particularly useful in various industrial domains. Even more interestingly, the bacteria, in addition to the above production capacity, exhibit one or more of the following properties:

It is extremophile,
It is viable at a pH comprised between 4 and 9,
It is viable in the presence of 2% ethanol,
It can be grown in aerobiosis or in anaerobiosis, and/or
It can utilize cellulose or a derivative thereof as carbon source.

This last property is particularly advantageous and unexpected. Indeed, the use of cellulose (or a derivative thereof) as sole carbon source requires an efficient enzymatic system comprising at least one cellobiase and one glucanase, and illustrates the ability of bacteria of this invention to grow under diverse industrial conditions.

Examples of cellulose derivatives include e.g., microcrystalline cellulose, hydroxypropyl cellulose, methylcellulose, hydroxypropylmethyl cellulose, ethylmethyl cellulose, powdered cellulose and cellulose wadding. Commercial sources of such cellulose or derivatives include Whatman paper, Avicelle (microcrystalline cellulose) or Solka Floc (powdered cellulose), for instance.

The ability of the present bacteria to use cellulose is illustrated e.g., by their unexpected capacity to grow on Whatman paper. This paper comprises cellulose or derivatives thereof and its use as carbon source and complete degradation requires an efficient enzymatic complex comprising exoglucanases, endoglucanases and cellobiases.

As a result, bacteria of this invention having the ability to utilize cellulose or Whatman paper as carbon source are expected to be able to grow on and/or transform a very large variety of substrates, including biomass, very efficiently. In this regard, it is striking to note that, among 200 tested new isolates of *Deinococcus* strains, 5 showed the ability to entirely degrade Whatman paper.

Therefore, strains of this invention not only exhibit remarkable properties for the production of metabolites, but they also grow on or can utilize particular substrates as carbon source, which makes them particularly advantageous for industrial use.

An object of this invention relates to an isolated stress-resistant bacterium, particularly a *Deinococcus* bacterium, wherein said bacterium can utilize cellulose as a carbon source to produce an organic acid or alcohol in aerobiosis. Preferred bacteria of this invention contain an efficient enzymatic system comprising at least one cellobiase and glucanase and are able to degrade cellulose (e.g., Whatman paper), preferably entirely.

Moreover, a preferred bacterium of this invention can further utilize additional substrates as carbon sources, particularly glucose, starch and sucrose. Preferred bacteria of this invention can also utilize carboxymethylcellulose, cellobiose, hemicellulose and xylose as carbon sources.

Another object of this invention is an isolated stress-resistant bacterium, particularly a *Deinococcus* bacterium, wherein said bacterium is thermophilic, viable at a pH comprised between 5 and 9, and produces at least 2 g/L lactate.

Another object of this invention is an isolated stress-resistant bacterium, particularly a *Deinococcus* bacterium, wherein said bacterium is thermophilic, viable at a pH comprised between 5 and 9, and produces at least 0.05 g/L of succinate.

Another object of this invention is an isolated stress-resistant bacterium, particularly a *Deinococcus* bacterium, wherein said bacterium is thermophilic, viable at a pH comprised between 5 and 9, and produces at least 0.25 g/L of acetate.

Another object of this invention is an isolated stress-resistant bacterium, particularly a *Deinococcus* bacterium, wherein said bacterium is thermophilic, viable at a pH comprised between 5 and 9, and produces at least 0.004% ethanol, preferably at least 0.04% ethanol.

As discussed above, preferred bacteria of the invention advantageously utilize cellulose as carbon source. They may, in addition, utilize other substrates such as glucose, starch and sucrose carboxymethylcellulose, cellobiose, hemicellulose and xylose.

The bacteria may be cultivated and/or maintained in any suitable culture medium and device. Examples of such medium include complex glucose medium or defined medium as disclosed in the examples. Suitable medium are also commercially available.

Specific examples of bacteria of this invention are *Deinococcus* strain M11-9D, deposited on May 7, 2009 at the CNCM under No. CNCM I-4155, *Deinococcus* strain MC2-2A, deposited on May 7, 2009, at the CNCM under No. CNCM I-4156, and *Deinococcus* strain M13-1A, deposited on May 7, 2009 at the CNCM under No. CNCM I-4157, or a derivative, mutant, transformant or progeny of said bacterium.

As disclosed in the examples, these deposited strains are all thermophilic, able to grow at a pH comprised between 5 and 9, and/or can utilize cellulose (as illustrated with Whatman paper) as carbon source.

MC2-2A has the remarkable ability to utilize a broad spectrum of substrates, such as CMC, cellobiose, xylan or xylose, and to produce valuable organic acids.

M13-1A has the unexpected ability to produce substantial levels of ethanol when cultured in the presence of Whatman paper as sole carbon source.

M119-D has the remarkable ability to produce more than 2.5 g/L of lactate, which is unprecedented for *Deinococcus* bacteria.

These bacteria of the present invention thus exhibit a combination of remarkable properties, in relation to substrate utilization and/or metabolite production, which are particularly useful for industrial purposes.

It should be understood that, using the teaching of the present invention and following experimental procedures as described e.g., in the experimental section, further stress-resistant bacteria, such as *Deinococcus* bacteria, having the properties according to this invention may be selected or isolated. In particular, now that the inventors have demonstrated the ability of certain stress-resistant bacteria to grow on Whatman paper, the skilled person, following the protocols provided in the experimental section, can isolate other strains having such property.

In this regard, a further object of this invention is a method of isolating a stress-resistant bacterium, particularly a *Deinococcus* bacterium, the method comprising:
 Providing a sample that potentially contains bacteria;
 Subjecting said sample to a DNA breaking treatment,
 Culturing said sample in the presence of cellulose or a derivative thereof (e.g., whatman paper), and
 Isolating growing or living bacteria from said culture.

Following this method, the inventors have isolated additional strains combining the above superior features. In particular, thermophilic *Deinococcus* strains, able to grow at a pH comprised between 5 and 9 and to produce above 0.3 g/L of lactate have been isolated, showing the utility of the above method.

Following the above method, the inventors have also been able to isolate additional thermophilic *Deinoccocus* strains able to grow at a pH comprised between 5 and 9 and to produce ethanol in culture with cellulose. Examples of such bacterium include:
 *Deinoccocus* M11 12B, which produces 0.041% ethanol in the presence of cellulose as the carbon source;
 *Deinoccocus* M14 6C, which produces 0.021% ethanol in the presence of cellulose as the carbon source; and
 *Deinoccocus* M13 8D, which produces 0.016% ethanol in the presence of cellulose as the carbon source.

The invention thus discloses several *Deinococcus* bacteria having the ability to use cellulose as carbon source. The invention discloses that such bacteria can produce ethanol using cellulose, under stressful culture conditions.

A further object of the invention is an extract of a bacterium as defined above. An "extract of a bacterium" designates any fraction obtained from a bacterium, such as a cell supernatant, cell debris, cell walls, DNA extract, enzymes or enzyme preparation or any preparation derived from bacteria by chemical, physical and/or enzymatic treatment, which is essentially free of living bacteria.

The invention also relates to derivatives, transformants, mutants or progeny of a bacterium as described above. The term transformant designates a strain which contains a recombinant nucleic acid (i.e., a nucleic acid that is not naturally present in said bacterium, or that has been altered or duplicated). The term mutant designates a strain which results from a mutagenic treatment. Derivatives designate any strain obtained from a strain of the present invention, e.g., by selection, which retains the ability to utilize the recited carbon source and to produce an organic acid or alcohol.

A further object of the invention relates to the use of a bacterium as defined above for producing an organic acid or alcohol.

A further object of the present invention relates to the use of a bacterium as defined above for producing bioalcohol, preferably ethanol.

The invention also relates to a method of producing an alcohol, preferably ethanol comprising cultivating a bacterium as defined above in the presence of an appropriate substrate, and collecting the alcohol.

The substrate may be any culture medium or various types of biomass or products derived therefrom. In particular, said acids and alcohols may be produced from renewable resources, especially plant or animal biomass, or from municipal and industrial wastes. Within the context of the present invention, the term "biomass" refers to living and dead biological material that can be used for industrial production. Most commonly, biomass refers to e.g., plant matter, animal matter, biodegradable wastes. Biomass can be derived from numerous types of plants, including miscanthus, switchgrass, hemp, sugarbeet, wheat, corn, poplar, willow, sorghum, sugarcane, and a variety of tree species, ranging from eucalyptus to oil palm. Biomass according to the invention can comprise raw biomass and/or secondary biomass. The raw biomass is unprocessed material from biological matter. Examples include forestry products, such as mature trees unsuitable for lumber or paper production, agricultural products, such as grasses, crops and animal manure, and aquatic products, such as algae and seaweed. The secondary biomass is any material initially derived from raw biomass, which has undergone significant chemical and physical changes. Examples include paper, leather, cotton, hemp, natural rubber products, food processing by-products, and used cooking oils.

A particular object of the invention relates to a method for producing a bio alcohol, comprising exposing a biomass to a bacterium of this invention, or an extract thereof, and, optionally, collecting the bioalcohol.

The bioalcohol is preferably ethanol.

The method of the invention may be performed in a reactor of conversion. By "reactor" is meant a conventional fermentation tank or any apparatus or system for biomass conversion specially designed to implement the invention and therefore consisting in particular of bioreactors, biofilters, rotary biological contactors, and other gaseous and/or liquid phase bioreactors, especially those adapted for the treatment of biomass or biomass derivatives. The apparatus which can be used according to the invention can be used continuously or in batch loads.

In the reactor, to implement the method of the invention, at least one bacterium of the invention, or bacterial extract thereof, is used, whilst said reactor is arranged and supplied so that physicochemical conditions are set up and maintained therein so that said bacterium is operational for the application under consideration and so that, optionally, bacterial growth is possible and preferably promoted therein.

The process may be conducted under aerobiosis, anaerobiosis or under microaerobiosis, depending on the substrate and bacterium.

Further aspects and advantages of the invention will be disclosed in the following examples, which should be considered as illustrative and do not limit the scope of this application.

EXAMPLES

Stress-resistant bacteria have been isolated from environmental samples. Bacteria having the unexpected ability to utilise particular carbon sources and to produce metabolites on interest have been identified and characterized. Examples of such strains have been deposited at the CNCM. The selection protocols and main properties of these bacteria are disclosed in this experimental section.

Example 1

Range of pH for Growth

Material and Methods
This method enables the evaluation of the ability of microorganisms to grow in a range of pH.

The test is to be carried out at 45° C. (Thermophilic strains).

Pre-culture (in stationary phase) prepared in Complex medium Glucose is centrifuged then washed three times with sterile osmosed water.

The washed culture is used to seed 200 µL PGY Medium (5% seeding). The test is done in 96 wells microplate.

PGY contains 10 g/L peptone, 5 g/L yeast extract, 1 g/L glucose.

pH is mastered with HCl 1M or NaOH 1M using a pH meter.

pH mastered media are filtered (0.2 µm).

Culture is performed in aerobiosis.

The microplate is left in an incubator, at 45° C., under agitation.

Effective growth result is determined after 7 and 14 days readings. Readings with the naked eye comparing with a positive and a negative control.

Results:

Isolated *Deinococcus* strains can grow in culture mediums which pH is between 5 and 9.

TABLE 1

Thermophilic *Deinococcus* strains: pH range for growth

| strains | species | growth temperature (° C.) | pH range (on PGY) |
|---------|---------|---------------------------|-------------------|
| MC2-2A  | D. geothermalis | 45 | 4-9 |
| M13-1A  | D. murrayi | 45 | 5-10 |
| M11-9D  | D. murrayi | 45 | 5-9 |

PGY: Peptone Glucose Yeast-extract

Example 2

Carbon Source Utilization

Material and Methods

This method enables the evaluation of the ability of microorganisms to use a carbon source of interest (Glucose, sucrose, starch, Whatman paper, CMC, cellobiose, hemi-cellulose, xylose) and to test a range of pH for growth.

The test is to be carried out at 45° C. (Thermophilic strains).

Pre-culture (in stationary phase) is prepared in Complex medium Glucose is centrifuged then washed three times with sterile osmosed water.

The washed culture is used to seed 200 µL Defined Medium. (5% seeding). The test is done in 96 wells microplate.

Defined medium is prepared with autoclaved osmosed water (15 minutes at 120° C.). To the autoclaved osmosed water are added the following solutions: MOPS buffer solution (10×) pH7 [acid MOPS 400 mM, $NH_4Cl$ 200 mM, NaOH 100 mM, KOH 100 mM, $CaCl_2$ 5 µM, $Na_2SO_4$ 2.76 mM, $MgCl_2$ 5.28 mM]; micronutrients (10000×) [$(NH_4)_6(Mo_7)24$ 300 mM, $H_3BO_3$ 4 mM, $CoCl_2$ 0.3 mM, $CuSO_4$ 0.1 mM, $MnCl_2$ 2.5 mM, $ZnSO_4$ 0.1 mM]; $FeCl_3$(100×) 2 mM in $C_6H_5Na_3O_7$ 20 mM; $K_2HPO_4$ 1 g/L: solutions sterilized by filtration (0.2 µm).

Carbon source: 10 g/L (except from starch 5 g/L and Hemi-cellulose 5 g/L)

Culture is performed in aerobiosis.

The microplate is left in an incubator, at 45° C., under agitation.

Effective growth result is determined after 7 and 14 days readings. Readings with the naked comparing with a positive and a negative control.

Results

The results show that strains can use Glucose, Sucrose, Starch, Whatman paper, CMC, Cellobiose, Hemi-cellulose as sole carbon source. These strains are particularly useful for second generation ethanol production. In particular, the results presented in Table 2 show that strain MC2-2A is able to utilize Glucose, Sucrose, Starch, Whatman paper, CMC, Cellobiose and Hemi-cellulose as carbon source.

TABLE 2

Thermophilic *Deinococcus* strains: Carbon source utilization under aerobiosis.

| strains | species | growth temperature (° C.) | pH range (on PGY) | Glucose, Sucrose, Starch | Whatman paper | CMC | Cellobiose | Xylan | Xylose | Lignin |
|---|---|---|---|---|---|---|---|---|---|---|
| MC2-2A | *D. geothermalis* | 45 | 4-9 | + | + | + | + | + | + | − |
| M13-1A | *D. murrayi* | 45 | 5-10 | + | + | − | − | − | − | − |
| M11-9D | *D. murrayi* | 45 | 5-9 | + | − | − | − | − | − | − |

PGY: Peptone Glucose Yeast-extract;
CM: Complex Medium

Further examples of thermophilic *Deinoccocus* strains able to grow at a pH comprised between 5 and 9 and to degrade cellulose isolated by the inventors include *Deinoccocus* M11 12B, *Deinoccocus* M14 6C; and *Deinoccocus* M13 8D.

Example 3

Metabolites Production—Complex Medium Glucose

Material and Methods

This method enables the evaluation of the ability of microorganisms to produce metabolites of interest from Complex medium glucose.

The test is carried out at 45° C. (Thermophilic strains).

From pre-cultures (in stationary phase) prepared in Complex medium Glucose, 6 ml of enriched medium are seeded (seeding at 1% v/v).

The enriched culture mediums tested are Complex Medium Glucose, Defined Medium Whatman paper.

Complex Medium Glucose contains: peptone 2 g/L, yeast extract 5 g/L and glucose 10 g/L in osmosed water: solution sterilized by autoclaving (15 minutes at 120° C.). To this solution are added the following solutions: MOPS buffer solution (10×) pH7 [acid MOPS 400 mM, $NH_4Cl$ 200 mM, NaOH 100 mM, KOH 100 mM, $CaCl_2$ 5 μM, $Na_2SO_4$ 2.76 mM, $MgCl_2$ 5.28 mM]; micronutrients (10000×) [$(NH_4)_6(Mo_7)24$ 300 mM, $H_3BO_3$ 4 mM, $CoCl_2$ 0.3 mM, $CuSO_4$ 0.1 mM, $MnCl_2$ 2.5 mM, $ZnSO_4$ 0.1 mM]; $FeCl_3$(100×) 2 mM in $C_6H_5Na_3O_7$ 20 mM; $K_2HPO_4$ 1 g/L: solutions sterilized by filtration (0.2 μm).

Cultures are performed both in aerobiosis and anaerobiosis (Biomerieux, Genbag).

Cultures in aerobiosis condition are left in an incubator, at 45° C., under agitation, for 7 days. The cultures are then centrifuged for 10 minutes at 4000 rpm. Supernatants are filtered (0.2 μm), poured into other tubes, and placed at −80° C.

Cultures in anaerobiosis condition are left in an incubator, at 45° C., for 4 weeks. The cultures are then centrifuged for 10 minutes at 4000 rpm. Supernatants are filtered (0.2 μm), poured into other tubes, and placed at −80° C.

Gas Chromatography FID analysis (Varian CP-WAX 57 CB 25 m*0.32 mm column) was used to quantify alcohols. Organic acids were quantified by Capillary Electrophoresis (5 mM 2,6-pyridinedicarboxylic acid 0.5 mM Cétyltrimèthylammonium bromide; 5.6 pH adjusted buffers/61 cm length, 50 μm diameter capillary Agilent). Residual glucose was quantified by HPLC coupled with refractometry (Phenomenex LUNA 3 u $NH_2$ 100A 150*4.6 mm column, $ACN/H_2O$ 85:15 mobile phase).

Results

Strains have been identified which can utilize Complex medium glucose in aerobiosis and anaerobiosis. This leads to interesting ethanol and acid production.

TABLE 3

Thermophilic *Deinococcus* strains: Metabolites production in Complex medium glucose under aerobiosis and anaerobiosis.

| | | | | Metabolites production CM Glucose aerobiosis | | | | | | |
|---|---|---|---|---|---|---|---|---|---|---|
| strains | species | growth temperature (° C.) | pH range (on PGY) | Acid production (g/L) | | | | | Ethanol (%) | residual glucose (g/L) |
| | | | | succinate | acetate | lactate | formate | malate | | |
| MC2-2A | *D. geothermalis* | 45 | 04-10 | 0 | 0.37 | 0.03 | 0.14 | 0 | 0 | 8.5 |
| M13-1A | *D. murrayi* | 45 | 05-10 | 0.25 | 0.25 | 0.17 | 0 | 0.03 | 0.011 | ND |
| M11-9D | *D. murrayi* | 45 | 05-10 | 0.06 | 0.48 | 2.65 | 0 | 0 | 0.016 | ND |

TABLE 3-continued

| | | growth temperature | pH range | Metabolites production CM Glucose anaerobiosis | | | | | | residual glucose |
|---|---|---|---|---|---|---|---|---|---|---|
| | | | | Acid production (g/L) | | | | | | |
| strains | species | (° C.) | (on PGY) | succinate | acetate | lactate | formate | malate | Ethanol (%) | (g/L) |
| MC2-2A | D. geothermalis | 45 | 04-10 | 0.2 | 0.04 | 0 | 0 | 0.12 | 0 | 9.7 |
| M13-1A | D. murrayi | 45 | 05-10 | ND | ND | ND | ND | ND | ND | ND |
| M11-9D | D. murrayi | 45 | 05-10 | 0.49 | 0.13 | 0.08 | 0 | 0.06 | 0 | 10 |

PGY: Peptone Glucose Yeast-extract
CM: Complex Medium

Example 4

Metabolites Production—Defined Medium Whatman Paper

This method enables the evaluation of the ability of microorganisms to produce metabolites of interest from Whatman paper utilization.

The test is carried out at 45° C. (Thermophilic strains).

Pre-cultures (in stationary phase) prepared in Complex medium Glucose are centriguged then washed three times with sterile osmosed water.

The washed cultures are used to seed 20 mL Defined Medium Whatman paper.

Defined Medium Whatman paper:
Defined medium is prepared with autoclaved osmosed water (15 minutes at 120° C.). To the autoclaved osmosed water are added the following solutions: MOPS buffer solution (10x) pH7 [acid MOPS 400 mM, $NH_4Cl$ 200 mM, NaOH 100 mM, KOH 100 mM, $CaCl_2$ 5 µM, $Na_2SO_4$ 2.76 mM, $MgCl_2$ 5.28 mM]; micronutrients (10000x) [$(NH_4)_6(Mo_7)24$ 300 mM, $H_3BO_3$ 4 mM, $CoCl_2$ 0.3 mM, $CuSO_4$ 0.1 mM, $MnCl_2$ 2.5 mM, $ZnSO_4$ 0.1 mM]; $FeCl_3$(100x) 2 mM in $C_6H_5Na_3O_7$ 20 mM; $K_2HPO_4$ 1 g/L: solutions sterilized by filtration (0.2 µm).
Carbon source: one Whatman filter paper N° 1 90 mm disk autoclaved (15 minutes, 120° C.) added to defined medium
Cultures are performed in aerobiosis.
Cultures in aerobiosis condition are left in an incubator, at 45° C., under agitation, for 6 weeks. The cultures are then centrifuged for 10 minutes at 4000 rpm. Supernatants are filtered (0.2 µm), poured into other tubes, and placed at −80° C. Gas Chromatography FID analysis (Varian CP-WAX 57 CB 25 m*0.32 mm column) was used to quantify alcohols. Organic acids were quantified by Capillary Electrophoresis (5 mM 2,6-pyridinedicarboxylic acid 0.5 mM Cétyltriméthylammonium bromide; 5.6 pH adjusted buffers/61 cm length, 50 µm diameter capillary Agilent). Residual glucose was quantified by HPLC coupled with refractometry (Phenomenex LUNA 3 u $NH_2$ 100A 150*4.6 mm column, ACN/$H_2O$ 85:15 mobile phase).

Results

Strains having the ability to utilize Whatman paper as sole carbon source under extremophile conditions have been identified. This degradation leads to interesting metabolite production.

TABLE 4

Thermophilic Deinococcus strains: Metabolites production from Whatman paper utilization under aerobiosis.

| | | growth temperature | pH range | Metabolites production whatman paper aerobiosis | | | | | |
|---|---|---|---|---|---|---|---|---|---|
| | | | | Acid production (g/L) | | | | | |
| strains | species | (° C.) | (on PGY) | succinate | acetate | lactate | formate | malate | Ethanol (%) |
| MC2-2A | D. geothermalis | 45 | 4-9 | 0 | 0 | 0 | 0 | 0 | 0 |
| M13-1A | D. murrayi | 45 | 5-10 | 0.07 | 0.26 | 0.08 | 0.5 | 0 | 0.049 |
| M11 12B | Deinococcus | 45 | 5-9 | nd | nd | nd | nd | nd | 0.041 |
| M14-6C | Deinococcus | 45 | 5-9 | n | nd | nd | nd | Nd | 0.021 |
| M13-8D | Deinococcus | 45 | 5-9 | nd | nd | nd | nd | nd | 0.016 |
| M11-9D | D. murrayi | 45 | 5-9 | No whatman paper degradation | | | | | |

PGY: Peptone Glucose Yeast-extract;
CM: Complex Medium

Example 5

Solvent Bactericidy

The ability of the bacteria of this invention to resist solvent exposure has been tested. This method enables evaluation of the micro-organism sensitivity to ethanol. The test is carried out at 45° C. (Thermophilic strains). Ethanol bactericidy is determined with ethanol added at:
T0,
exponential phase,
stationary phase.
For ethanol bactericidy at T0, ethanol percentages between 0 to 10% are tested.

From a pre-culture in stationary phase in an enriched culture medium, for each ethanol content to be tested, 200 µl of Complex medium Glucose is seeded at 1% v/v.

Complex Medium Glucose contains: peptone 2 g/L, yeast extract 5 g/L and glucose 10 g/L in osmosed water: solution sterilized by autoclaving (15 minutes at 120° C.). To this solution are added the following solutions: MOPS buffer solution (10×) pH7 [acid MOPS 400 mM, $NH_4Cl$ 200 mM, NaOH 100 mM, KOH 100 mM, $CaCl_2$ 5 µM, $Na_2SO_4$ 2.76 mM, $MgCl_2$ 5.28 mM]; micronutrients (10000×) [$(NH_4)_6(Mo_7)24$ 300 mM, $H_3BO_3$ 4 mM, $CoCl_2$ 0.3 mM, $CuSO_4$ 0.1 mM, $MnCl_2$ 2.5 mM, $ZnSO_4$ 0.1 mM]; $FeCl_3$(100×) 2 mM in $C_6H_5Na_3O_7$ 20 mM; $K_2HPO_4$ 1 g/L: solutions sterilized by filtration (0.2 µm).

The test is performed in 96 wells microplates in aerobiosis. Ethanol evaporation is avoided using a sterile impermeable film.

The reading of the result is done by naked eye.

Results:

The concentration of solvent at which we consider there is a loss of bacterial viability corresponds to the minimum concentration of solvent at which we observe total growth inhibition.

The strains tested present satisfactory resistance to the solvents from the perspective of an industrial application in a fermenter (cf table 5).

Ethanol Bactericidy at Exponential and Stationary Phases

Test:

From a pre-culture in stationary phase in an enriched culture medium, for each ethanol content to be tested, 5 mL of Complex medium Glucose is seeded at 1% v/v.

Complex Medium Glucose contains: peptone 2 g/L, yeast extract 5 g/L and glucose 10 g/L in osmosed water: solution sterilized by autoclaving (15 minutes at 120° C.). To this solution are added the following solutions: MOPS buffer solution (10×) pH7 [acid MOPS 400 mM, $NH_4Cl$ 200 mM, NaOH 100 mM, KOH 100 mM, $CaCl_2$ 5 µM, $Na_2SO_4$ 2.76 mM, $MgCl_2$ 5.28 mM]; micronutrients (10000×) [$(NH_4)_6(Mo_7)24$ 300 mM, $H_3BO_3$ 4 mM, $CoCl_2$ 0.3 mM, $CuSO_4$ 0.1 mM, $MnCl_2$ 2.5 mM, $ZnSO_4$ 0.1 mM]; $FeCl_3$(100×) 2 mM in $C_6H_5Na_3O_7$ 20 mM; $K_2HPO_4$ 1 g/L: solutions sterilized by filtration (0.2 µm).

A follow-up of growth is carried out using the control culture (no ethanol add neither at exponential phase nor at stationary phase). OD is read at 600 nm using a spectrophotometer (UV Light XS5, SECOMAM).

Once the exponential growth phase (optical density of 0.5 at 600 nm), or once the stationary phase (plateau), is reached, the solvent is added. The content tested is 0 to 20%. Then, cultures are incubated during 2 hours.

At the end of the incubation period and for each ethanol content tested, a count is taken to assess the influence of the ethanol on the strain.

Count: At the end of incubation, and for each concentration in solvent, 200 µL of culture are transferred onto another microplate and are diluted in cascade (dilutions at ¹⁄₁₀ over 9 wells). The dilution culture medium is an enriched medium. 5 µL of each dilution are laid in triplicate on PGY agar medium. peptone 5 g/L, yeast extract 2.5 g/L, glucose 0.5 g/L, agar 14 g/L: medium sterilized by autoclaving 20 minutes at 120° C. Once growth permits, for each percentage of solvent tested, a count is carried out to evaluate the influence of organic solvents on the strain.

Results:

The concentration of solvent at which we consider there is a loss of bacterial viability corresponds to the minimum concentration of solvent at which we observe the loss of one log in relation to the control.

The strains tested present an excellent resistance to the solvents from the perspective of an industrial application in a fermenter (cf table 5).

TABLE 5

Thermophilic *Deinococcus* strains: ethanol bactericidy

| strains | species | growth temperature (° C.) | pH range (on PGY) | Ethanol Bactericidy | | |
|---------|---------|--------------------------|-------------------|---------------------|------------------|------------------|
| | | | | T0 | Exponential phase | Stationary phase |
| MC2-2A | *D. geothermalis* | 45 | 4-9 | 5% | 15% | 15% |
| M13-1A | *D. murrayi* | 45 | 5-10 | 2.5% | 5% | ND |
| M11-9D | *D. murrayi* | 45 | 5-9 | ND | ND | ND |

PGY: Peptone Glucose Yeast-extract;
CM: Complex Medium

CNCM Deposit

*Deinococcus* bacteria MC2-2A, M13 1A and M11 9D have been deposited at the CNCM under the Budapest treaty.

M11-9D has been deposited on May 7, 2009 at the CNCM under No. CNCM I-4155, *Deinococcus* strain MC2-2A has been deposited on May 7, 2009, at the CNCM under No. CNCM I-4156, and *Deinococcus* strain M13-1A has been deposited on May 7, 2009 at the CNCM under No. CNCM I-4157. The expert solution has been requested.

The invention claimed is:

1. An isolated stress-resistant *Deinococcus* bacterium, wherein said bacterium exhibits cellobiase, endoglucanase and exoglucanase activities, and produces at least 0.015% ethanol when cultured in aerobiosis in the presence of cellulose or a derivative thereof as a sole carbon source.

2. The bacterium of claim 1, wherein said bacterium produces at least 0.04% ethanol when cultured in aerobiosis in the presence of cellulose or a derivative thereof as a sole carbon source.

3. The bacterium of claim 1, wherein said bacterium is thermophilic and viable at a pH comprised between 5 and 9.

4. The bacterium of claim 1, wherein said bacterium produces lactate.

5. The bacterium of claim 1, wherein said bacterium produces succinate.

6. The bacterium of claim 1, wherein said bacterium produces acetate.

7. The bacterium of claim 1, wherein said bacterium utilizes glucose, starch and/or sucrose as a carbon source.

8. The bacterium of claim 1, wherein said bacterium utilizes xylose as a carbon source.

9. The bacterium of claim 1, wherein said bacterium grows at a temperature of 45° C. or more.

10. The bacterium of claim 1, wherein said bacterium is selected from a strain of *D. radiodurans, D. geothermalis, D. murrayi, D. cellulosilyticus* or *D. deserti*.

11. A bacterium selected from *Deinococcus* strain M11-9D deposited on May 7, 2009 at the CNCM under No. CNCM I-4155, *Deinococcus* strain MC2-2A deposited on May 7, 2009, at the CNCM under No. CNCM I-4156, and *Deinococcus* strain M13-1A deposited on May 7, 2009 at the CNCM under No. CNCM I-4157, or a derivative, mutant, transformant or progeny of said bacterium.

12. A method of producing an alcohol comprising cultivating a bacterium of claim 1 in the presence of an appropriate carbon source, and collecting the alcohol.

13. The bacterium of claim 1, wherein said cellulose derivative is selected from microcrystalline cellulose, hydroxypropyl cellulose, methylcellulose, hydroxypropylmethyl cellulose, ethylmethyl cellulose, powdered cellulose, cellulose wadding, carboxymethylcellulose, cellobiose, or hemicellulose.

14. A method of producing ethanol, comprising (i) cultivating a bacterium of claim 1 in the presence of cellulose or a derivative thereof selected from microcrystalline cellulose, hydroxypropyl cellulose, methylcellulose, hydroxypropylmethyl cellulose, ethylmethyl cellulose, powdered cellulose, cellulose wadding, carboxymethylcellulose, cellobiose, or hemicellulose, and (ii) collecting ethanol.

15. The method of claim 12, wherein said alcohol is ethanol, butanol, propanol, methanol, isopropanol, propanediol, glycerol, or 2-3 butane diol.

16. The method of claim 12, wherein said alcohol is ethanol.

* * * * *

UNITED STATES PATENT AND TRADEMARK OFFICE
CERTIFICATE OF CORRECTION

PATENT NO. : 8,728,777 B2  
APPLICATION NO. : 13/320048  
DATED : May 20, 2014  
INVENTOR(S) : Jacques Biton and Cathy Isop Page 1 of 1

It is certified that error appears in the above-identified patent and that said Letters Patent is hereby corrected as shown below:

In the Specification,

Column 7,
Line 40, "on interest" should read --of interest--.

Column 13,
Line 43, "add" should read --added--.
Lines 57-59, "medium.peptone 5g/L, yeast extract 2.5 g/L, glucose 0.5 g/L, agar 14 g/L: medium sterilized by autoclaving 20 minutes at 120°C." should read --medium (peptone 5g/L, yeast extract 2.5 g/L, glucose 0.5 g/L, agar 14 g/L: medium sterilized by autoclaving 20 minutes at 120°C).--.

In the Claims,

Column 14,
Lines 60-61, "or a derivative, mutant, transformant or progeny" should read --or a transformant or progeny--.

Signed and Sealed this
Twentieth Day of January, 2015

Michelle K. Lee
*Deputy Director of the United States Patent and Trademark Office*